United States Patent
Zawada et al.

(10) Patent No.: US 7,033,511 B2
(45) Date of Patent: Apr. 25, 2006

(54) SUSTAINED WATER TREATMENT IN DENTAL EQUIPMENT

(75) Inventors: Jeffrey A. Zawada, Lake Oswego, OR (US); Clayton L. D. Moore, Sr., Tualatin, OR (US)

(73) Assignee: A-DEC, Inc., Newberg, OR (US)

(*) Notice: Subject to any disclaimer, the term of this patent is extended or adjusted under 35 U.S.C. 154(b) by 0 days.

(21) Appl. No.: 10/761,926

(22) Filed: Jan. 20, 2004

(65) Prior Publication Data

US 2005/0155937 A1 Jul. 21, 2005

(51) Int. Cl.
*C02F 1/50* (2006.01)
(52) U.S. Cl. ............... 210/764; 252/175; 252/186.1; 422/28
(58) Field of Classification Search ............. 210/758, 210/759, 764; 252/175, 186.1; 422/28; 424/409
See application file for complete search history.

(56) References Cited

U.S. PATENT DOCUMENTS

| | | | |
|---|---|---|---|
| 2,105,835 A | 1/1938 | Krause | |
| 2,320,280 A | 5/1943 | Kalusdian | |
| 2,396,515 A | 3/1946 | Kreidl et al. | |
| 2,917,428 A | 12/1959 | Hitzman | |
| 4,043,932 A | 8/1977 | Fresenius et al. | |
| 4,545,956 A | 10/1985 | Ciszewski et al. | |
| 4,686,060 A | 8/1987 | Crabtree et al. | |
| 4,847,089 A | 7/1989 | Kramer et al. | |
| 4,915,955 A | 4/1990 | Gömöri | |
| 4,923,619 A | 5/1990 | Legros | |
| 4,941,989 A | 7/1990 | Kramer et al. | |
| 5,017,295 A | 5/1991 | Antelman | |
| 5,073,382 A * | 12/1991 | Antelman | 424/604 |
| 5,217,626 A | 6/1993 | Yahya et al. | |
| 5,223,149 A | 6/1993 | Antelman | |
| 5,320,805 A | 6/1994 | Kramer et al. | |
| 5,620,527 A | 4/1997 | Kramer et al. | |
| 5,837,204 A | 11/1998 | Prevost et al. | |
| 5,977,183 A * | 11/1999 | Scepanski | 514/643 |
| 6,019,905 A * | 2/2000 | Waggoner | 210/739 |
| 6,242,002 B1 | 6/2001 | Tritthart et al. | |
| 6,267,885 B1 | 7/2001 | Briggs et al. | |
| 6,267,895 B1 | 7/2001 | Engelhard et al. | |
| 6,325,944 B1 | 12/2001 | DeSanto | |
| 6,419,850 B1 | 7/2002 | Rouleau | |
| 6,544,427 B1 | 4/2003 | Layton | |
| 6,555,055 B1 * | 4/2003 | Cisar et al. | 422/28 |
| 6,610,275 B1 * | 8/2003 | Owades et al. | 424/55 |
| 2002/0148789 A1 | 10/2002 | Layton | |
| 2003/0003013 A1 | 1/2003 | Castellini | |
| 2004/0108271 A1 | 6/2004 | Downs | |
| 2004/0217326 A1 * | 11/2004 | Souler et al. | 252/179 |

FOREIGN PATENT DOCUMENTS

| | | |
|---|---|---|
| DE | 41 37 544 | 5/1993 |
| EP | 0 059 978 | 9/1982 |
| EP | 0 059 978 B1 | 6/1984 |
| EP | 0 720 814 | 7/1996 |
| EP | 1 266 571 | 12/2002 |
| EP | 1 389 470 A1 | 2/2004 |
| GB | 353409 | 2/1930 |
| GB | 421692 | 12/1932 |
| GB | 927540 | 5/1963 |
| GB | 1421417 | 1/1976 |
| GB | 2 268 879 | 1/1994 |
| GB | 2355198 A | 4/2001 |
| GB | 2355408 A | 4/2001 |
| JP | 55-013228 A2 | 1/1980 |
| JP | 2001017452 | 1/2001 |
| WO | WO 91/08981 | 6/1991 |
| WO | WO 96/04935 A1 | 2/1996 |
| WO | WO 99/18790 | 4/1999 |
| WO | WO 02/081378 A1 | 10/2002 |
| WO | WO 02/081378 A1 | 10/2002 |

OTHER PUBLICATIONS

"AIREL: Infection General Neutralizer (I.G.N.)," 10 pages, 1988.
Alliger, "An Overall View of $ClO_2$," Frontier Pharmaceutical, Inc., 17 pages, Aug. 2001.
"ALPRO® Report," 4 pages, Jan. 14, 1999.
"ALPRO® Packaging," 2 pages.
"Dental Unit Waterlines: Approaching the Year 2000," by the ADA Council on Scientific Affairs, JADA, vol. 130, pp. 1653-1663, Nov. 1999.
"DioxiClear™ Dental Line Cleaner," Frontier Pharmaceutical, Inc., 4 pages, Aug. 2001.
"EC Material Safety Data Sheet according to 91/1551 EWG," Alpron Safety Data Sheet, 3 pages, Jul. 17, 2000.

(Continued)

*Primary Examiner*—Betsey Morrison Hoey
(74) *Attorney, Agent, or Firm*—Klarquist Sparkman,LLP

(57) ABSTRACT

An antimicrobial composition, methods of making the composition, and methods of using the composition. The composition comprises a substantially dry mixture of effective amounts of one or more quaternary ammonium compounds, one or more oxidizing agents, and one or more antimicrobial metallic compounds, such as silver-containing compounds. The composition is primarily directed to the sustained treatment of dental unit water.

66 Claims, No Drawings

OTHER PUBLICATIONS

"Effer-Soda™ Soda Bicarbonate," http://www.spipharma.com/ProductsFolder/117EfferSoda/117EfferSoda.html, 3 pages, website visited on Jan. 28, 2004.

"Feature/Benefit Analysis of KOTP Traditional Unit," 1 page, Mar. 2001.

"Federal Register: Rules and Regulations," vol. 63, No. 241, pp. 69403-69405, Dec. 1998.

Marshall, "Section 3: Compression/ Compaction," FMC, 46 pages, Aug. 1999.

"Metasys Information," 2 pages, Sep. 2001.

"MicroCLEAR™ Information," 7 pages, 2000.

Propst, "FMC BioPolymer—Problem Solver: Tablet Processing," http://www.fmcbiopolymer.com/Content/BIO/Images/Section%202%20Tablet%20Processing.pdf, 22 pages, Dec. 23, 2002.

Puttaiah, et al., "Utilization of Two Concentrations of $ClO_2$ Cleaner in Controlling Dental Waterline Contamination," Frontier Pharmaceuticals, Inc., Farmingdale, NY, 2 pages, Aug. 2001.

"Research Report Summary: Rowpar® Dental Unit Waterline Cleaner," 3 pages, 2000.

Shearer, "Biofilm and the Dental Office," JADA, vol. 127, pp. 181-189, Feb. 1996.

Smith et al, "Evaluation of the Efficacy of Alpron Disinfectant for Dental Unit Water Lines," British Dental Journal, vol. 193, No. 10, pp. 593-596, Nov. 2002.

"Sterilex® Ultra Powder," 10 pages, Jun. 9, 2003.

"Sterisil™: PureTube™" packaging, 5 pages.

Wehling, "Effervescent Technology Adds Sparkle to Supplements," Nutrition Industry Executive website, http://www.vitaminretailer.com/SIE/articles/EffervescentTechnology.htm, 6 pages, website visited on Jan. 19, 2004.

Williams, et al., "Microbial Contamination of Dental Unit Waterlines: Origins and Characteristics," Compendium, vol. 17, No. 6, 13 pages, Jun. 1996.

Williams, et al., "Microbial Contamination of Dental Unit Waterlines: Current Preventive Measures and Emerging Options," Compendium, vol. 17, No. 7, 12 pages, Jul. 1996.

European Search Report (EP05100291.3).

McDowell et al., "A Simulated-Use Evaluation of a Strategy for Preventing Biofilm Formation in Dental Unit Waterlines," JADA, 135:799-805 (Jun. 2004).

Green&Clean WK, Solution for Decontamination of Water and the Hose System in Dental Units, Safety Data Sheet issued Oct. 7, 1997, METASYS Medizintechnik GmbH (4pp).

* cited by examiner

SUSTAINED WATER TREATMENT IN DENTAL EQUIPMENT

FIELD

This disclosure relates to compositions and methods for treating water, particularly for water used in traditional dental practices.

BACKGROUND

Microbial contamination of dental unit water recently has been recognized as a serious health concern. Dental unit water systems provide an environment conducive to the growth of a variety of microorganisms. Many dental units provide water from a water reservoir. This water passes through narrow tubes and then into a patient's mouth during treatment. Patients are exposed to the water during rinsing procedures and may also ingest small amounts during treatment. The water is typically stored at room temperature or heated slightly. The characteristic low flow-rates, warm temperatures, and high ratios of surface-area-to-volume all promote microbial growth.

The health effects of exposure to microbial contamination from dental unit water systems have not been determined. It is well known, however, that contamination of drinking water can have adverse health consequences. While dental unit water is not consumed in large quantities, its use may be a factor when such consequences arise. The risks are especially acute for people with compromised immune systems. Plus, even patients who would not be affected by contaminated water may prefer to be treated with disinfected water. Clearly, efforts to disinfect dental unit water systems are warranted.

Contamination of dental unit water systems occurs within the water itself and on surfaces exposed to the water. These types of contamination are related, because microbes from the surfaces are introduced into the water and microbes from the water adhere to the surfaces. In general, the microbial concentrations will be much greater on the surfaces than in the water. Many types of microbes purposefully anchor themselves to solid surfaces by excreting a sticky polysaccharide material. This anchoring process is done in order to facilitate propagation. The surface propagation of these organisms is difficult to avoid. Once some microbes have become anchored to a surface, colonies will begin to form. Eventually, the surfaces will become coated with a layer of biological material referred to as a "biofilm."

Biofilms are especially difficult to remove from the surfaces within dental units that cannot be exposed and cleaned manually (e.g., the inner surface of tubing). Passing a disinfecting fluid through the system will not necessarily destroy the biofilm, in part because some microbes are shielded by the constituent polysaccharide material and/or other microbes.

Several products have been developed in an effort to remove biofilms from dental unit water systems. These products use certain compounds to penetrate the biofilms and expose them to antimicrobial agents. Such products include Ultra®, which is manufactured by the Sterilex Corporation and Dentacide®, which is manufactured by Frio Technologies. Most of these products are designed to be introduced into the system overnight and flushed in the morning. They are not designed for continuous daily use and/or patient treatment use. These "shock products" are often slightly toxic and would be unpleasant and/or harmful if ingested by patients. Periodic disinfection of the system with shock products is time consuming and inadequate. There is a need for compositions directed to the sustained disinfection of dental unit water and the inhibition of biofilm growth.

Conventional compositions for disinfecting dental unit water have included a variety of compounds. For example, U.S. Pat. No. 6,544,427 discloses the use of colloidal silver and U.S. Pat. No. 6,419,850 discloses the use of EDTA, benzalkonium chloride, and sodium tosylchloramide. In addition to disinfecting compositions, conventional disinfecting methods and devices include, among others, in-line filtration and purge systems.

Conventional compositions, methods, and devices are all deficient in at least one significant respect. For example, some conventional compositions include only one class of antimicrobial agent. These compositions have diminished antimicrobial effectiveness because some organisms may be resistant to that particular class of antimicrobial agent.

There is a need for improved compositions, methods, and devices for the disinfection of dental unit water.

SUMMARY

Compositions are disclosed for the disinfection of dental unit water as well as methods for making and using these compositions. The compositions comprise three main agents: (1) one or more quaternary ammonium compounds; (2) one or more oxidizing agents; and (3) one or more antimicrobial metallic compounds. These agents were selected based on a variety of factors, including one or more of the following: antimicrobial effectiveness, duration of antimicrobial effectiveness, compatibility with existing equipment, cost, ease of use, human toxicity, effect on dentin bonding, resistance to heat, and/or shelf-life, depending on the particular implementation.

Disclosed embodiments of the composition may be provided as powders or in solution, but working embodiments were provided in tablet form. In addition to the three main antimicrobial agents, the compositions also may include one or more chelating/coordinating compounds, such as tetrasodium ethylene diamine tetracitric acid ("tetrasodium EDTA"), citric acid, sodium citrate, etc., as well as combinations of these compounds.

The embodiments may also include materials useful for forming acceptable compositions and/or tablets, including flow aids, inert materials, coloring agents, flavoring agents, binders, etc., and combinations thereof. To promote dissolution of the tablet, the compositions may also include one or more effervescing or disintegrating agents.

One embodiment of the disclosed compositions comprises from about 0.2% to about 40% by weight, typically from about 0.5% to about 20% by weight, of a quaternary ammonium compound; from about 0.2% to about 20% by weight as active oxygen, typically from about 0.5% to about 3% by weight as active oxygen, of an oxidizing agent; and from about 0.02% to about 1.5% by weight as silver, typically from about 0.05% to about 0.5% by weight as silver, of a silver compound as an antimicrobial metallic compound.

Methods for using the composition also are disclosed. Some methods comprise providing an embodiment of the composition and then introducing it, along with water to be treated, into a dental unit reservoir.

Some methods result in dental unit water comprising from about 0.2 mg/L to about 20 mg/L, typically from about 0.5 mg/L to about 10 mg/L, of a quaternary ammonium compound; from about 0.2 mg/L to about 20 mg/L as active oxygen, typically from about 0.5 mg/L to about 3 mg/L as active oxygen, of an oxidizing agent; and from about 0.02 mg/L to about 1.5 mg/L as silver, typically from about 0.05 mg/L to about 0.5 mg/L as silver, of a silver compound.

The composition and methods are compatible with concurrent use of a shock treatment, such as, e.g., Ultra® or Dentacide®.

Of course the disclosed compositions could also be used for applications outside the field of treating water used for dental applications.

Methods for making the composition also are disclosed. One method for making the composition includes providing at least the quaternary ammonium compound, the oxidizing agent, and the antimicrobial metallic compound and forming at least these ingredients into a tablet.

DETAILED DESCRIPTION

The following definitions are solely to aid readers and are no narrower than the meaning of the terms as understood by a person skilled in the art.

As used herein, the term "biofilm" refers to biological material adhering to a surface, including adhesion matrices associated with the biological material.

As used herein, the term "disinfect" means to reduce or substantially eliminate the biological effects of some portion of the biological material present in a liquid or on a surface.

As used herein, the term "dental unit" refers to any device or portion thereof typically used in dental procedures that incorporates water in one or more of its functional features.

As used herein, the term "microbe" refers to one or more biological agents, including without limitation: bacteria, viruses, fingi, spores, molds, yeasts, etc., and combinations thereof.

As used herein, the term "shock treatment" refers to methods of treating dental unit water systems comprising introducing an antimicrobial composition to the system and then flushing at least a portion to substantially all of that composition from the system. The system is then refilled with water for patient treatment. Shock treatments are generally designed for periodic use. The shock-treated water is generally not intended for human consumption.

As used herein, the term "tablet" refers to a generally cohesive structure comprising an effective amount of a composition that is easily separable from other tablets.

As used herein, the term "chelating/coordinating compound" refers to a compound that associates with and/or binds to free metal ions in solution.

Described herein are embodiments of compositions for applications including, but not limited to disinfecting dental unit water, as well as methods for making and using such compositions. The disinfecting activity of the disclosed embodiments results in part from the individual and combined disinfecting properties of three components: (1) a quaternary ammonium compound; (2) an oxidizing agent; and (3) an antimicrobial metallic compound.

I. Quaternary Ammonium Compound

The disclosed embodiments comprise a quaternary ammonium compound or other compound having the same effects. Quaternary ammonium compounds are ammonium salts in which all four of the ammonium's hydrogen atoms have been replaced by organic groups. The quaternary ammonium compounds of the present disclosure have the following basic structure:

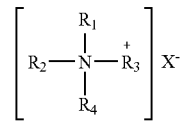

wherein $R_1$, $R_2$, $R_3$, and $R_4$ are organic substituent groups that provide the quaternary ammonium compound with antimicrobial properties and X is any anion that makes the compound sufficiently water soluble to allow the compound to form an antimicrobial solution. With reference to this general formula, $R_1$, $R_2$, $R_3$, and $R_4$ are typically independently selected from the group consisting of all alkyl groups and aryl groups.

The antimicrobial activity of quaternary ammonium compounds may be related to their ability to disrupt the cell membranes of microbes. It is suspected that positively charged quaternary ammonium ions are attracted to the net negative charge on the surface of most microbes. The preferred quaternary ammonium compounds of the present disclosure release a positively charged quaternary ammonium ion in solution.

The antimicrobial activity of quaternary ammonium compounds is enhanced where the quaternary ammonium ion has a hydrophobic portion. Therefore, the preferred quaternary ammonium compounds of the present disclosure have at least one substituent group containing from 6 to 24 carbon atoms, typically from 8 to 20 carbon atoms; or, alternatively, two substituent groups that form an aliphatic or aromatic ring including the nitrogen atom.

The disclosed embodiments may contain an effective amount of a single quaternary ammonium compound or mixtures of two or more quaternary ammonium compounds. Examples of quaternary ammonium compounds suitable for the disclosed embodiments include without limitation: n-alkyl dimethyl benzyl ammonium chloride, n-alkyl dimethyl ethylbenzyl ammonium chloride, n-alkyl dimethyl 3,4-dichlorobenzyl ammonium chloride, dioctyl dimethyl ammonium chloride, didecyl dimethyl ammonium chloride, cetyl pyridinium chloride, etc., and combinations thereof.

II. Oxidizing Agent

An oxidizing agent is any substance that oxidizes another substance and is thereby reduced. Microbes can be killed by oxidation, so oxidizing agents have antimicrobial properties. Some preferred oxidizing agent(s) release hydrogen peroxide or a peroxyacid in solution. Other preferred oxidizing agent(s) do not contain chlorine. Compounds from the preferred classes of oxidizing agents have been found to be effective when used in conjunction with the other components of the disclosed embodiments. These compounds are also generally stable in dry form and have relatively low human toxicity. For example, oxidizing agents without chlorine do not form toxic trihalomethanes in solution. A variety of oxidizing agents, however, may be successfully incorporated in the disclosed embodiments, including compounds that do not release hydrogen peroxide or a peroxyacid in solution and compounds that contain chlorine.

The disclosed embodiments may contain an effective amount of a single oxidizing agent or mixtures of two or more oxidizing agents. Examples of oxidizing agents suitable for the disclosed embodiments include, without limitation: sodium percarbonate, potassium peroxymonosulfate, sodium perborate monohydrate, sodium perborate hexahydrate, calcium hypochlorite, calcium peroxide, magnesium peroxide, urea peroxide, sodium chlorite, sodium dichloroisocyanurate, etc., and combinations thereof. Sodium percarbonate has been found to be an especially advantageous oxidizing agent.

III. Antimicrobial Metallic Compound

Certain metals are generally toxic to microorganisms and make good antimicrobial agents. These antimicrobial metallic compounds include silver compounds, copper compounds, and zinc compounds. While a variety of antimicrobial metallic compounds can be incorporated into the present invention, silver compounds are preferred. Compared to copper and zinc, a lower concentration of silver is needed to produce an equivalent antimicrobial effect. Silver has some human toxicity, but the concentration necessary to impart antimicrobial activity to dental unit water is very low.

In dry form, the antimicrobial metallic compound of the present disclosure can be in colloidal form or bound within one or more salts or compounds. Metallic salts are preferred because they are generally more effective at lower concentrations.

The disclosed embodiments may contain an effective amount of a single antimicrobial metallic compound or mixtures of two or more antimicrobial metallic compounds. Examples of silver compounds suitable for the disclosed embodiments include without limitation: silver nitrate, silver nitrite, silver citrate, silver phosphate, silver benzoate, silver acetate, silver chlorate, silver chlorite, silver perchlorate, silver fluoride, silver sulfate, colloidal silver, etc., and combinations thereof.

IV. Combinations

The three antimicrobial components discussed above were selected for their individual and combined properties when applied to the sustained disinfection of dental unit water. Individually, each component has a specific antimicrobial action. The combination of these three components enhances the overall effectiveness of the composition by providing multiple disinfection mechanisms. For example, certain microbes that may be resistant to quaternary ammonium compounds may not be resistant to oxidizing agents and/or antimicrobial metallic compounds. The overall composition is expected to be effective against a wide range of microbes.

Each of the antimicrobial components discussed above also has a specific duration of effectiveness. The combination of the three components takes advantage of these differences to create a suitable temporal spectrum of activity, and hence allows formation of a composition with sustained antimicrobial activity. Oxidizing agents produce a strong, rapid antimicrobial effect, but this effect may not persist over an extended period of time. In contrast, many antimicrobial metallic compounds remain in solution and have sustained antimicrobial action for a substantially indefinite period. More like antimicrobial metallic compounds, quaternary ammonium compounds will actively disinfect for a substantially indefinite period after being introduced into solution, albeit at a slower rate than typical oxidizing agents.

The antimicrobial effect of the disclosed compositions can be characterized by an initial effect that gradually decreases and is followed by a sustained effect. Dental unit water is usually changed once a day and, since sterile water is rarely used, microbe concentrations may vary over a wide range when the water is initially introduced. The disclosed composition has a strong initial antimicrobial effect, so the water in the dental unit can be used almost immediately after the composition is introduced. Little or no waiting is required before the microbial contamination is sufficiently reduced.

Sustained disinfection of water in dental unit water systems can be distinguished from shock treatment in that sustained disinfection does not require that the water supply system be flushed after treatment. Sustained disinfection involves treating the same water to which patients are exposed during dental procedures. In general, sustained disinfection is more preventative than corrective. The present composition is well-suited to sustained disinfection partially because it has low toxicity and yet still effectively prevents the growth of biofilms.

The ability of one embodiment of the present composition to prevent the growth of biofilms was confirmed by the experiment disclosed in Example 2. Thus, using the composition on a regular basis will eliminate, or at least reduce, the need for shock treatment.

Many factors other than antimicrobial effectiveness and biofilm inhibition were considered in selecting composition components. These additional factors include compatibility with existing equipment, cost, ease of use, human toxicity, effect on dentin bonding, resistance to heat, and shelf-life. The same factors also were considered in formulating preferred concentration ranges for the antimicrobial components.

The ingredients used to form the composition are provided in amounts effective to inhibit deleterious health effects that may result from administering microbe-contaminated dental water to a subject. For working embodiments, these amounts were as follows: from about 0.2% to about 40% by weight, typically from about 0.5% to about 20% by weight, of a quaternary ammonium compound; from about 0.2% to about 20% by weight as active oxygen, typically from about 0.5% to about 3% by weight as active oxygen, of an oxidizing agent; and from about 0.02% to about 1.5% by weight as silver, typically from about 0.05% to about 0.5% by weight as silver, of a silver compound. These concentration ranges are expected to result in the optimum antimicrobial activity in light of the limiting factors. The preferred concentration ranges can be broadened to account for the many types of filler and other additives that can be incorporated into the composition.

In some disclosed embodiments, it is advantageous to combine the three main antimicrobial agents discussed above with one or more chelating/coordinating compounds, such as tetrasodium EDTA and/or citrate ion (e.g. from citric acid). The purpose of including a chelating/coordinating compound is to sequester ions that may interfere with or compromise the activity of the active agents. For example, stray metal ions might reduce the effectiveness of the quaternary ammonium compound or be oxidized by the oxidizing agent. In some embodiments, the chelating/coordinating compound is present at concentrations of about 2% to about 75% by weight.

The incorporation of citric acid is especially advantageous. Citric acid forms citrate ion in solution. Citrate ion is a chelating compound and it loosely binds silver, which is the preferred antimicrobial metal. This interaction helps keep the silver in solution and thus facilitates silver's antimicrobial activity. In testing, citric acid was also found to improve the shelf-life and stability of the composition. Citric acid is also useful for creating effervescence, which is discussed below in greater detail.

The overall composition may be provided in a dry form, such as tablet form or powder form. The dry form improves the shelf-life of the product. The tablet form is preferred because it also facilitates correct dosing and generally makes the product easier to use. In order to hold the ingredients in a cohesive tablet form, one or more binders may be used. Suitable binders include, but are not limited to: carbohydrates (including, without limitation, sorbitol, microcrystalline cellulose, lactose, dextrose monohydrate, sucrose, sugar, starch, etc.), gelatin, waxes, natural gums, synthetic gums, polyols (particularly polyalkylene glycols, such as polyethylene glycol and polypropylene glycol), polyvinylpyrrolidone, sodium alginate, dicalcium phosphate, tricalcium phosphate, calcium sulfate, etc., and combinations thereof. In the tablet embodiments, the binder, if necessary, is present in an amount suitable to impart the composition with some cohesion. This effect can be achieved at concentrations of 1% to 25% by weight, and more typically at concentrations of 2% to 12% by weight.

To promote dissolution of tablet embodiments in solution, one or more effervescing and/or disintegrating compounds may be included in the composition. Effervescing compounds release gas bubbles that disrupt the tablet structure and promote mixing. Disintegrating compounds swell or otherwise enable water to penetrate the tablet and promote its disintegration.

Suitable disintegrating agents include, without limitation: carbohydrates (including, without limitation, starches, celluloses, etc.), aluminum oxide, polyvinylpyrrolidone, etc., and combinations thereof. Most effervescing agents take the form of two or more compounds that react in water. Suitable effervescent agents include, without limitation, the combination of (1) perborates, percarbonates, carbonates, bicarbonates, sesquicarbonates, etc., and combinations thereof with (2) an acid, including, without limitation, citric acid, tartaric acid, lactic acid, sulphamic acid, gluconic acid, malic acid, maleic acid, fumaric acid, succinic acid, glutaric acid, adipic acid, acetic acid, phosphoric acid, etc., and combinations thereof.

Effervescing agents are typically more effective than disintegrating agents at quickly preparing a homogeneous solution with little or no agitation. Since it is difficult to agitate dental unit water within a dental unit reservoir, effervescing agents are preferred.

The disintegrating or effervescing agent, if used, is present in an amount suitable to facilitate dissolution of the tablet. For disintegrating agents this effect can be achieved at concentrations of 0.5% to 30% by weight, and more typically at concentrations of 2% to 20% by weight. For effervescing agents this effect can be achieved at concentrations of 1% to 99% by weight, and more typically 10% to 90% by weight.

Embodiments of the present composition may affect the pH of the solution into which they are mixed. For example, some embodiments incorporate citric acid, which affects the pH of the solution into which it is mixed. The pH of the solution formed by introducing embodiments of the present composition in water is typically about 4 to about 8, and is preferably slightly acidic. The preferred pH ranges have been found to make the solution more compatible with dental equipment and to improve the palatability of the solution to patients.

The tablet embodiments of the disclosed composition are made by a tablet-forming process. Suitable tablet-forming processes include wet granulation, dry granulation, and direct compression. An example of a tablet-forming process for an effervescing tablet is found in U.S. Pat. No. 6,242,002. In some tablet-forming processes, it is advantageous to provide a set of ingredients with a substantially uniform particle-size distribution. See Marshall, Keith, *Problem Solver and Reference Manual, Compression/Compaction*, 2003 (online version). Additional tablet-forming details are provided in *DI Pharm Tech, Training Volume I*, 2003, *The Manufacturing Process*, Westminster, S.C., DI Pharma Tech, 2003. Also see Propst, Cecil W., *Problem Solver and Reference Manual, Tablet Processing*, 2002 (online version).

Tablet-forming processes generally include preparing the ingredients, blending the ingredients, and compressing the ingredients into a tablet form. During processing, care should be taken to prevent the premature reaction and/or degradation of the ingredients. For example, the highly reactive ingredients may need to be blended separately from the other ingredients. Some ingredients also may need to be dried before being combined with the other ingredients. See Effer-Soda Soda Bicarbonate (no date, available at www.spipharma.com).

Environmental conditions may need to be controlled to preserve one or more of the ingredients. For example, dehumidification of the manufacturing atmosphere may be required. In addition, the antimicrobial metallic compound and the finished tablets may need to be protected from light. For additional details regarding the control of environmental conditions see Marshall, Keith, *Problem Solver and Reference Manual, Compression/Compaction*, 2003 (online version). Also see Wehling, Fred, *Effervescing Technology Adds Sparkle to Supplements* (no date, available at www.vitaminretailer.com).

In tablet embodiments, one or more lubricating agents may be incorporated into the composition. The lubricating agent facilitates the manufacture of the tablets by certain tablet-forming processes. Specifically, the lubricating agent facilitates the release of the tablets from a conventional tablet press. Suitable lubricating agents include, but are not limited to: polyols (particularly polyalkylene glycols, such as polyethylene glycol and polypropylene glycol), sodium oleate, sodium stearate, magnesium stearate, calcium stearate, stearic acid, sodium stearyl fumarate, sodium benzoate, sodium acetate, sodium chloride, hydrogenated vegetable oils, mineral oil, etc., and combinations thereof. The lubricating agent, if used, is present in an amount suitable to facilitate the smooth and complete release the tablet from the tablet press. This effect can be achieved at concentrations of 0.1% to 10% by weight, and more typically at concentrations of 0.2% to 5% by weight. It is, of course, also possible to provide lubrication in other ways, such as, e.g., by lubricating the tablet producing equipment.

V. In Use

Some embodiments of the disclosed composition are used by simply dropping one tablet, multiple tablets, or any fraction(s) thereof into a dental unit reservoir that contains water to be used during treatment. The water may be supplied from the local water supply (e.g., from a municipal water supply or a well) or from another source, e.g., bottled water. Alternatively, the composition can be introduced into the reservoir before or simultaneously with the water. In embodiments that include an effervescing agent, little or no agitation should be necessary to achieve dissolution of the composition within the water. Typically, this process is repeated as needed, or each time the reservoir is refilled, which is usually about once daily.

The present composition is primarily directed to the sustained treatment of dental unit water. Experimental results, including the results stated in Example 2, suggest that daily use of the present composition will eliminate or at least reduce the need for shock treatments. In some cases, however, it may be advantageous to use the present composition in conjunction with shock treatments. Shock treatments, for example, can hasten removal of existing contamination on the surfaces of dental unit systems.

In addition to its primary use for the sustained disinfection of dental unit water, the present composition can also be used as an agent for shock treatment. For example, the present composition can be introduced into a dental unit water system at a concentration higher than the concentration typically used for the sustained treatment of dental water. The dental water containing higher concentrations of the present composition can then be flushed from the system before refilling the system with water for patient treatment. After a shock treatment is performed, the sustained disinfection provided by the present composition will help maintain the low levels of microbial contamination.

The appropriate amount of the disclosed composition to be used depends upon the desired concentrations of the antimicrobial components in the dental unit water, the quantity of water present in the reservoir, as well as other possible factors. This amount of composition can be translated into an appropriate tablet size and/or an appropriate number of tablets (or fractions thereof). The resulting preferred concentration ranges in the dental water being treated are: 0.2 mg/L to about 20mg/L, typically from about 0.5mg/L to about 10 mg/L, of quaternary ammonium compound; from about 0.2 mg/L to about 20 mg/L as active oxygen, typically from about 0.5 mg/L to about 3 mg/L as active oxygen of oxidizing agent; and, in embodiments including silver compounds, from about 0.02 mg/L to about 1.5 mg/L as silver, typically from about 0.05 mg/L to about 0.5 mg/L as silver of silver compound. Considering that most dental unit reservoirs have a capacity between 0.7 and 2 Liters, the preferred tablet size used to provide these concentration ranges is about 20 mg to 500 mg, typically about 50 mg to 250 mg.

EXAMPLES

The following examples are provided to illustrate certain particular embodiments of the disclosure. It should be understood that additional embodiments not limited to the particular features described are consistent with the following examples.

Example 1

This working example describes a tablet embodiment of the disclosed antimicrobial composition suited for the sustained disinfection of dental unit water. The quaternary ammonium compound in this embodiment comprised a mixture of n-alkyl dimethyl benzyl ammonium chloride (20 weight %), n-alkyl dimethyl ethylbenzyl ammonium chloride (20 weight %) and inert ingredients (60 weight %). The oxidizing agent comprised sodium percarbonate in dry powder form with a fine particle size. The antimicrobial metallic compound comprised silver nitrate with a fine particle size.

In addition to the three main antimicrobial components, the antimicrobial composition of this working example also comprised tetrasodium EDTA dihydrate, sorbitol, polyethylene glycol, sodium benzoate, citric acid, and sodium bicarbonate.

The ingredients in the antimicrobial composition of this working example were present in the following concentrations: sodium percarbonate (8.19 weight %); sorbitol (10.00 weight %); sodium bicarbonate (24.98 weight %); tetrasodium EDTA dihydrate (9.42 weight %); citric acid (40.02 weight %); quaternary ammonium compound mixture (4.25 weight %); silver nitrate (0.14 weight %); polyethylene glycol (1.00 weight %); and sodium benzoate (2.00 weight %).

Example 2

This example describes one experiment that was performed to establish the effectiveness of the composition described in Example 1. The results of this experiment confirm that treating dental unit water with the composition described in Example 1 dramatically reduces microbial contamination and inhibits biofilm growth.

Ten identical dental-unit water systems were provided. Each dental-unit water system included a reservoir, tubing, a control system, and other typical dental-unit water system components. The dental-unit water systems were programmed to simulate typical dental-unit water system use. During the experiment, each dental-unit water system was programmed to perform 10 dispensing periods per day. During each dispensing period, approximately 60 mL of water was dispensed. Additional water was dispensed during flushing cycles performed before the first dispensing period each day and between each successive dispensing period.

Each weekday during the experiment, the reservoirs of five of the dental-unit water systems were filled with distilled water buffered with a 1:100 dilution of phosphate buffered saline. These five dental-unit water systems will be referred to as the "buffered distilled water group." The reservoirs of the remaining five dental-unit water systems were filled with the same solution, but with the water hardness adjusted to at least 200 mg/L as $CaCO_3$. These five dental-unit water systems will be referred to as "the hard water group." The solutions used to fill the reservoirs were inoculated with common strains of bacteria to achieve contamination levels of approximately $10^2$–$10^3$ colony-forming units per milliliter (CFU/mL). Three of the five dental-unit water systems in the "buffered distilled water group" and "the hard water group" were treated with an effervescing tablet, as described in Example 1. The remaining two dental-unit water systems in each group served as controls.

On the first weekday of each week of the experiment, before refilling the reservoirs, microbial contamination was measured. This measurement was performed by dispensing equal volumes of water from each dental-unit water system via the handpiece water coolant tubing. The outside of the each handpiece was disinfected with isopropyl alcohol before the samples were taken. The samples were treated with sodium thiosulfate and sodium thioglycolate to eliminate any remaining antimicrobial activity and were then spread onto Agar plates. The plates were incubated at room temperature and then the colonies were counted. Table 1 shows the experimental results. Note that no data was collected for the treated dental-unit water systems at the beginning of week two.

TABLE 1

Heterotrophic Plate Count Analysis of Water Sampled from Handpiece Water Coolant Tubing at the Start of Each Test Week

| Buffered Distilled Water Group | | | Hard Water Group | | |
|---|---|---|---|---|---|
| | Heterotrophic Plate Count, log (CFU/mL) | | | Heterotrophic Plate Count, log (CFU/mL) | |
| Time, weeks | Untreated | Treated with Test Composition | Time, weeks | Untreated | Treated with Test Composition |
| 0 | 1.87 | <0.05 | 0 | 1.98 | <0.05 |
| 1 | 3.76 | <0.05 | 1 | 5.97 | <0.05 |
| 2 | 4.85 | N/A | 2 | 6.59 | N/A |
| 3 | 4.20 | <0.05 | 3 | 6.28 | <0.05 |
| 4 | 2.85 | <0.05 | 4 | 6.74 | <0.05 |
| 5 | 5.16 | <0.05 | 5 | 6.75 | <0.05 |

TABLE 1-continued

Heterotrophic Plate Count Analysis of Water Sampled from Handpiece
Water Coolant Tubing at the Start of Each Test Week

| Buffered Distilled Water Group | | | Hard Water Group | | |
|---|---|---|---|---|---|
| | Heterotrophic Plate Count, log (CFU/mL) | | | Heterotrophic Plate Count, log (CFU/mL) | |
| Time, weeks | Untreated | Treated with Test Composition | Time, weeks | Untreated | Treated with Test Composition |
| 6 | 3.17 | <0.05 | 6 | 5.72 | <0.05 |
| 7 | 2.90 | <0.05 | 7 | 6.63 | <0.05 |
| 8 | 5.17 | <0.05 | 8 | 6.92 | <0.05 |
| 9 | 5.06 | <0.05 | 9 | 7.02 | <0.05 |
| 10 | 4.64 | <0.05 | 10 | 7.02 | <0.05 |
| 11 | 5.67 | <0.05 | 11 | 7.01 | <0.05 |
| 12 | 5.60 | <0.05 | 12 | 6.77 | <0.05 |
| 13 | 5.55 | <0.05 | 13 | 6.78 | <0.05 |
| 14 | 5.58 | <0.05 | 14 | 6.34 | <0.05 |
| 15 | 5.50 | <0.05 | 15 | 6.58 | <0.05 |
| 16 | 5.91 | <0.05 | 16 | 5.99 | <0.05 |

Table 1 shows that microbial contamination increased for the untreated dental-unit water systems over the course of the study. This increase can be attributed to the proliferation of the bacteria introduced into the system and the associated growth of biofilms. In contrast, the treated dental-unit water systems showed virtually no microbial contamination. It can be concluded that treatment effectively destroyed the bacteria introduced into the system and inhibited the growth of biofilms. The effectiveness of the treatment was not found to be dependent on water hardness.

The ability of the tested water treatment to inhibit biofilm growth was also verified visually. At the end of weeks 10 and 16, a portion of the tubing from the treated and untreated test groups was subjected to scanning electron microscope (SEM) analysis. The SEM analysis showed that a biofilm was present on the inside of the tubing from the untreated dental-unit water systems and that no biofilm was present on the inside of the tubing from the treated dental-unit water systems.

Although specific embodiments of the compositions have been described as comprising effective amounts of a quaternary ammonium compound, an oxidizing agent and an antimicrobial metallic compound, other suitable compositions may comprise (1) a quaternary ammonium compound, an oxidizing agent and citric acid, (2) a quaternary ammonium compound, an antimicrobial metallic compound and citric acid, or (3) an oxidizing agent, an antimicrobial metallic compound and citric acid.

Although the embodiments described above primarily relate to the treatment of water used in dentistry related applications, the same compositions can be used in other types of water and surface treatment applications. Other embodiments of the invention will be apparent to those of ordinary skill in the art from a consideration of this specification, or practice of the invention disclosed herein. It is intended that the specification and examples be considered as exemplary only, with the true scope and spirit of the invention being indicated by the following claims.

We claim:

1. An antimicrobial composition for sustained treatment of dental unit water comprising a substantially dry mixture of effective amounts of a quaternary ammonium compound, an oxidizing agent, a silver compound, and citric acid.

2. The composition of claim 1, wherein the quaternary ammonium compound is selected from the group consisting of n-alkyl dimethyl benzyl ammonium chloride, n-alkyl dimethyl ethylbenzyl ammonium chloride, n-alkyl dimethyl 3,4-dichlorobenzyl ammonium chloride, dioctyl dimethyl ammonium chloride, didecyl dimethyl ammonium chloride, cetyl pyridinium chloride, and combinations thereof.

3. The composition of claim 1, wherein the quaternary ammonium compound is present in a concentration of about 0.2% to about 40% by weight.

4. The composition of claim 1, wherein the quaternary ammonium compound is present in a concentration of about 0.5% to about 20% by weight.

5. The composition of claim 1, wherein the oxidizing agent forms hydrogen peroxide or a peroxyacid in solution.

6. The composition of claim 1, wherein the oxidizing agent is selected from the group consisting of sodium percarbonate, potassium peroxymonosulfate, sodium perborate monohydrate, sodium perborate hexahydrate, calcium peroxide, magnesium peroxide, urea peroxide, and combinations thereof.

7. The composition of claim 1, wherein the oxidizing agent comprises sodium percarbonate.

8. The composition of claim 1, wherein the oxidizing agent is present in a concentration of about 0.2% to about 20% by weight as active oxygen.

9. The composition of claim 1, wherein the oxidizing agent is present in a concentration of about 0.5% to about 3% by weight as active oxygen.

10. The composition of claim 1, wherein the silver compound is selected from the group consisting of silver nitrate, silver nitrite, silver citrate, silver phosphate, silver benzoate, silver acetate, silver chlorate, silver chlorite, silver perchlorate, silver fluoride, silver sulfate, colloidal silver, and combinations thereof.

11. The composition of claim 1, wherein the silver compound is present in a concentration of about 0.02% to about 1.5% by weight as silver.

12. The composition of claim 1, wherein the silver compound is present in a concentration of about 0.05% to about 0.5% by weight as silver.

13. The composition of claim 1, wherein the citric acid is present in a concentration of about 2% to about 75% by weight.

14. The composition of claim 1, wherein the composition is in tablet form.

15. The composition of claim 14, wherein the quaternary ammonium compound is selected from the group consisting of n-alkyl dimethyl benzyl ammonium chloride, n-alkyl dimethyl ethylbenzyl ammonium chloride, n-alkyl dimethyl 3,4-dichlorobenzyl ammonium chloride, dioctyl dimethyl ammonium chloride, didecyl dimethyl ammonium chloride, cetyl pyridinium chloride, and combinations thereof.

16. The composition of claim 14, wherein the oxidizing agent forms hydrogen peroxide or a peroxyacid in solution.

17. The composition of claim 14, wherein the oxidizing agent is selected from the group consisting of sodium percarbonate, potassium peroxymonosulfate, sodium perborate monohydrate, sodium perborate hexahydrate, calcium peroxide, magnesium peroxide, urea peroxide, and combinations thereof.

18. The composition of claim 14, wherein the oxidizing agent comprises sodium percarbonate.

19. The composition of claim 14, wherein the silver compound is selected from the group consisting of silver nitrate, silver nitrite, silver citrate, silver phosphate, silver benzoate, silver acetate, silver chlorate, silver chlorite, silver perchlorate, silver fluoride, silver sulfate, colloidal silver, and combinations thereof.

20. The composition of claim 14, wherein the oxidizing agent reacts with citric acid in solution to produce effervescence.

21. An antimicrobial composition for sustained treatment of dental unit water comprising a substantially moisture-free mixture of effective amounts of a quaternary ammonium compound, an oxidizing agent, a silver compound, and citric acid.

22. An antimicrobial composition comprising:
from about 0.2% to about 40% by weight of a quaternary ammonium compound;
from about 0.2% to about 20% by weight as active oxygen of an oxidizing agent;
from about 0.02% to about 1.5% by weight as silver of a silver compound; and
from about 2% to about 75% by weight of citric acid.

23. The composition of claim 22, wherein the composition is in tablet form.

24. A method for causing sustained antimicrobial activity in a water supply comprising:
providing a substantially dry composition comprising effective amounts of a quaternary ammonium compound, an oxidizing agent, a silver compound, and citric acid; and
forming a mixture comprising water and said composition.

25. The method of claim 24, wherein the mixture comprises:
from about 0.2 mg/L to about 20 mg/L of quaternary ammonium compound;
from about 0.2 mg/L to about 20 mg/L as active oxygen of oxidizing agent;
from about 0.02 mg/L to about 1.5 mg/L as silver of the silver compound; and
from about 2% to about 75% by weight of the citric acid.

26. The method of claim 24, wherein the mixture comprises:
from about 0.5 mg/L to about 10 mg/L of the quaternary ammonium compound;
from about 0.5 mg/L to about 3 mg/L as active oxygen of the oxidizing agent;
from about 0.05 mg/L to about 0.5 mg/L as silver of the silver compound; and
from about 2% to about 75% by weight of the citric acid.

27. A method for causing sustained antimicrobial activity in a water supply comprising:
providing a substantially dry composition comprising effective amounts of a quaternary ammonium compound, an oxidizing agent, and an antimicrobial metallic compound; and
forming a mixture comprising water and said composition, wherein the mixture is formed in a dental unit reservoir.

28. The method of claim 27, further comprising cleaning biofilm from the dental unit before forming the mixture in the dental unit reservoir.

29. The method of claim 28, wherein cleaning biofilm from the dental unit comprises performing a shock treatment.

30. The method of claim 27, further comprising maintaining the microbial contamination in the dental unit reservoir at less than 0.05 log (CFU/mL) for at least five consecutive days.

31. The method of claim 27, wherein forming the mixture comprises adding the composition to the dental unit reservoir once daily for at least five consecutive days.

32. The method of claim 27, further comprising substantially inhibiting the growth of biofilm in a dental unit water system connected to the dental unit reservoir.

33. The method of claim 27, wherein the composition is in tablet form.

34. The method of claim 27, wherein the mixture is acidic.

35. The method of claim 27, wherein the composition further comprises citric acid.

36. The method of claim 35, wherein the oxidizing agent reacts with the citric acid in solution to produce effervescence.

37. A method for causing sustained antimicrobial activity in a water supply comprising:
providing a substantially dry composition comprising effective amounts of a quaternary ammonium compound, an oxidizing agent, and an antimicrobial metallic compound;
forming a mixture comprising water and said composition; and
introducing the mixture into a dental unit reservoir.

38. The method of claim 37, further comprising cleaning biofilm from the dental unit before introducing the mixture into the dental unit reservoir.

39. The method of claim 38, wherein cleaning biofilm from the dental unit comprises performing a shock treatment.

40. The method of claim 37, further comprising maintaining the microbial contamination in the dental unit reservoir at less than 0.05 log (CFU/mL) for at least five consecutive days.

41. The method of claim 37, further comprising substantially inhibiting the growth of biofilm in a dental unit water system connected to the dental unit reservoir.

42. The method of claim 37, wherein the composition is in tablet form.

43. The method of claim 37, wherein the mixture is acidic.

44. The method of claim 37, wherein the composition further comprises citric acid.

45. The method of claim 44, wherein the oxidizing agent reacts with the citric acid in solution to produce effervescence.

46. A method for causing sustained antimicrobial activity in a water supply comprising:
providing a substantially dry composition comprising effective amounts of a quaternary ammonium compound, an oxidizing agent, and an antimicrobial metallic compound;
forming a mixture comprising water and said composition; and
performing a dental treatment on a patient in which the patient comes in contact with the mixture.

47. The method of claim 46, wherein the composition is in tablet form.

48. The method of claim 46, wherein the mixture is acidic.

49. The method of claim 46, wherein the composition further comprises citric acid.

50. The method of claim 49, wherein the oxidizing agent reacts with the citric acid in solution to produce effervescence.

51. A method for causing sustained antimicrobial activity in a dental unit water supply comprising:
providing a tablet comprising effective amounts of a quaternary ammonium compound, an oxidizing agent, a silver compound, and citric acid; and forming a mixture comprising water and at least a portion of the tablet.

52. The method of claim 51, wherein forming a mixture includes adding at least a portion of the tablet to a dental unit reservoir, further comprising allowing the mixture to effervesce.

53. The method of claim 52, wherein the mixture is ready for use in dental treatment within fifteen minutes after adding at least a portion of the tablet to the dental unit reservoir.

54. The method of claim 51, wherein the mixture is formed in a dental unit reservoir.

55. The method of claim 54, further comprising cleaning biofilm from the dental unit before forming the mixture in the dental unit reservoir.

56. The method of claim 55, wherein cleaning biofilm from the dental unit comprises performing a shock treatment.

57. The method of claim 51, further comprising introducing the mixture into a dental unit reservoir.

58. The method of claim 57, further comprising cleaning biofilm from the dental unit before introducing the mixture into the dental unit reservoir.

59. The method of claim 58, wherein cleaning biofilm from the dental unit comprises performing a shock treatment.

60. The method of claim 51, further comprising performing a dental treatment on a patient in which the patient comes in contact with the mixture.

61. The method of claim 51, wherein the mixture comprises:
   from about 0.2 mg/L to about 20 mg/L of a quaternary ammonium compound;
   from about 0.2 mg/L to about 20 mg/L as active oxygen of an oxidizing agent; and
   from about 0.02 mg/L to about 1.5 mg/L as silver of a silver compound.

62. The method of claim 51, wherein the mixture comprises:
   from about 0.5 mg/L to about 10 mg/L of a quaternary ammonium compound;
   from about 0.5 mg/L to about 3 mg/L as active oxygen of an oxidizing agent; and
   from about 0.05 mg/L to about 0.5 mg/L as silver of a silver compound.

63. The method of claim 51, wherein the mixture is acidic.

64. The method of claim 51, further comprising maintaining the microbial contamination in the dental unit water supply at less than 0.05 log (CFU/mL) for at least five consecutive days.

65. The method of claim 51, wherein the oxidizing agent reacts with the citric acid in solution to produce effervescence.

66. A method for making a composition comprising:
   providing a quaternary ammonium compound;
   providing an oxidizing agent;
   providing a silver compound;
   providing citric acid; and
   forming at least the quaternary ammonium compound, oxidizing agent, silver compound, and citric acid into a tablet.

* * * * *

UNITED STATES PATENT AND TRADEMARK OFFICE
CERTIFICATE OF CORRECTION

PATENT NO. : 7,033,511 B2
APPLICATION NO. : 10/761926
DATED : April 25, 2006
INVENTOR(S) : Jeffrey A. Zawada et al.

It is certified that error appears in the above-identified patent and that said Letters Patent is hereby corrected as shown below:

In the Specification:
Column 3, line 34, "fingi" should read --fungi--.

Signed and Sealed this

Sixth Day of March, 2007

JON W. DUDAS
*Director of the United States Patent and Trademark Office*